(12) United States Patent
Bjaerum et al.

(10) Patent No.: US 6,579,240 B2
(45) Date of Patent: Jun. 17, 2003

(54) ULTRASOUND DISPLAY OF SELECTED MOVEMENT PARAMETER VALUES

(75) Inventors: Steinar Bjaerum, Horten (NO); Bjorn Olstad, Stathelle (NO); Kjell Kristoffersen, Oslo (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/064,083

(22) Filed: Jun. 10, 2002

(65) Prior Publication Data

US 2003/0013962 A1 Jan. 16, 2003

Related U.S. Application Data

(60) Provisional application No. 60/297,572, filed on Jun. 12, 2001.

(51) Int. Cl.$^7$ ................................................ A61B 8/12
(52) U.S. Cl. ..................................... 600/447; 600/456
(58) Field of Search ............................. 600/455, 440, 600/441, 443, 453, 456, 454, 442, 437

(56) References Cited

U.S. PATENT DOCUMENTS

| | | |
|---|---|---|
| 5,628,321 A | 5/1997 | Scheib et al. |
| 5,820,561 A | 10/1998 | Olstad et al. |
| 5,846,202 A | 12/1998 | Ramamurthy et al. |
| 5,910,119 A | 6/1999 | Lin |
| 5,921,931 A * | 7/1999 | O'Donnell et al. ......... 600/441 |
| 6,110,119 A * | 8/2000 | Hall ........................... 600/455 |
| 6,120,451 A * | 9/2000 | Washburn et al. .......... 600/454 |

* cited by examiner

Primary Examiner—Marvin M. Lateef
Assistant Examiner—Maulin Patel
(74) Attorney, Agent, or Firm—McAndrews, Held & Malloy, Ltd.; Peter J. Vogel; Michael A. Dellapenna

(57) ABSTRACT

An ultrasound machine is disclosed that generates a color representation of moving structure, such as a cardiac wall tissue within a region of interest, and is displayed on a monitor. The color representation is generated by displaying at least one color characteristic related to a movement parameter of the structure, such as mean velocity or mean strain rate. The related feature of the movement parameter is mapped to the color characteristic by an apparatus comprising a front-end that generates received signals in response to backscattered ultrasound waves. A Doppler processor generates a set of parameter signals representing a spatial set of values of the movement parameter within the structure. A host processor embodies a tracking function and a peak-detection function to generate a set of tracked movement parameter profiles and a set of peak values of the movement parameter over a time period corresponding to anatomical locations within the region of interest. The set of peak values of the movement parameter are then mapped to a set of color characteristic signals. A display processor applies the mapped values of the color characteristic signals to the set of peak values of the movement parameter, representing the moving structure, to display a color representation, on a monitor.

20 Claims, 7 Drawing Sheets

Fig. 3

105
MYOCARDIUM TISSUE STRUCTURE

APICAL 4-CHAMBER VIEW OF HEART

TVI IMAGE

85
COLOR CHARACTERISTIC LEGEND

- $+V_{NYQUIST}$ [CM/S]
- 84 POSITIVE SEGMENT
- 0 CM/S
- 82 NEGATIVE SEGMENT
- $-V_{NYQUIST}$ [CM/S]

Fig. 4

APICAL 4-CHAMBER VIEW OF HEART

TVI IMAGE

- $+SR_{PEAK}$ [1/S]
- 0 [1/S]
- $-SR_{PEAK}$ [1/S]

ULTRASOUND DISPLAY OF SELECTED MOVEMENT PARAMETER VALUES

CROSS REFERENCE TO RELATED APPLICATIONS

The applicants claimed priority based on provisional application No. 60/297,572 filed Jun. 12, 2001 in the names of Bjorn Olstad, Steinar Bjaerum, and Kjell Kristoffersen.

BACKGROUND OF INVENTION

Certain embodiments of the present invention relate to an ultrasound machine for displaying an image of moving structure. More particularly, certain embodiments relate to displaying a color characteristic representing the moving structure.

Echocardiography is a branch of the ultrasound field that is currently a mixture of subjective image assessment and extraction of key quantitative parameters, of cardiac wall function has been hampered by a lack of well-established parameters that may be used to increase the accuracy and objectivity in the assessment of, for example, coronary artery diseases. Stress echo is such an example. It has been shown that the subjective part of wall motion scoring in stress echo is highly dependent on operator training and experience. It has also been shown that inter-observer variability between echo-centers is unacceptably high due to the subjective nature of the wall motion assessment.

Much technical and clinical research has focused on the problem and has aimed at defining and validating quantitative parameters. Encouraging clinical validation studies have been reported, which indicate a set of new potential parameters that may be used to increase objectivity and accuracy in the diagnosis of, for instance, coronary artery diseases. Many of the new parameters have been difficult or impossible to assess directly by visual inspection of the ultrasound images generated in real-time. The quantification has typically required a post-processing step with tedious, manual analysis to extract the necessary parameters.

Much of the prior art describes techniques for color mapping of estimated imaging parameters such as tissue velocity and strain rate. A fixed mapping of a continuous range of color hues is typically used to indicate positive velocities or strain rates and a second fixed mapping of a continuous range of color hues is used to indicate negative velocities or strain rates. This type of color encoding makes it easy to identify reversals in velocities or strain rates. Timing information related to the velocity or strain rate reversals is also easy to extract from M-mode displays.

However, the tissue velocity imaging (TVI) and strain rate imaging (SRI) modes and associated color mapping schemes in the prior art are not, by themselves, well suited for visual determination of other parameters, such as "peak" mean velocities or "peak" mean strain rates over a portion of the cardiac cycle. Herein, "peak" refers to the largest mean parameter value within a set of mean parameter values. Typically, a Nyquist velocity and associated pulse repetition frequency is set in order to avoid aliasing. Most of the actual mean velocities are only a small fraction of the peak mean velocity that, in cardiac imaging from apex, typically may be measured at the mitral ring during the E-wave in diastole. As a result, most regions in the image are colored with only small variations of the color hue selected for lower positive and/or lower negative mean velocities. Quantitative assessment of parameters such as peak mean velocities or peak mean strain rates from 2-D images has been difficult, even in lucky situations, with a good spread of measured imaging parameters. It has, therefore, been necessary to resort to post-processing techniques and manual extraction of the digital information for estimation of quantitative peak values.

Academic work has been done for validation of peak mean systolic velocities as an indicator of, for example, ischemia in stress echo. Clinical results indicate that a reduction in peak mean systolic velocities at peak exercise is a good predictor of coronary artery diseases. Therefore, it is useful to design a display mechanization that makes it easy to visually assess above average and/or peak mean systolic velocities in a quantitative manner.

U.S. Pat. No. 5,820,561 (Olstad, et al, issued Oct. 13, 1998) describes extracting timing information from estimated parameters (such as velocity of curved organs) during a cardiac cycle and color encoding the timing information for display.

U.S. Pat. No. 5,910,119 (Lin, issued Jun. 8, 1999) describes a technique for computing and displaying the absolute magnitude and direction of peak velocities for tissue using variance estimates.

U.S. Pat. No. 5,628,321 (Scheib, et al., issued May 13, 1997) describes a technique for computing many peak velocities over a cardiac cycle from the power spectrum of received pulses using a threshold to determine an optimum cardiac cycle.

U.S. Pat. No. 5,846,202 (Ramamurthy, et al, issued Dec. 8, 1998) describes color coding of blood flow velocities and using the highest mean velocity for display (Col 9, lines 7–14).

Techniques described in the foregoing patents fail to provide a color coded display of moving structure from which a user may readily observe peak structural movement parameter values.

A need exists for a robust approach to easily visualize a color-coded display of moving tissue structure such that a user may readily observe structural movement parameter values that are larger than mean values.

SUMMARY OF INVENTION

An embodiment of the present invention provides an ultrasound system for generating an image representative of moving cardiac structure by displaying color characteristics representative of peak values of mean parameter signals that are representative of the moving structure.

An apparatus is provided in an ultrasound machine for generating a display responsive to moving structure of a subject within a region of interest (ROI) by displaying at least one color characteristic related to a movement parameter of the structure. In such an environment the apparatus for displaying the color characteristic preferably comprises a front-end arranged to transmit ultrasound waves into the structure and then to generate received signals in response to ultrasound waves backscattered from the structure in the ROI over a time period. A processor is responsive to the received signals to generate a set of parameter signals representing values of the movement parameter within the structure during the time period and is responsive to the set of parameter signals to generate a color characteristic signal representative of a selected value larger than the mean value of the set of parameter signals. A display is arranged to display a color representation of the moving structure in response to the color characteristic signal.

A method is also provided in an ultrasound machine for generating a display responsive to moving structure within a region of interest (ROI) of a subject by displaying at least one color characteristic related to a movement parameter of the structure. In such an environment, the method preferably comprises transmitting ultrasound waves into the structure and receiving signals in response to ultrasound waves backscattered from the structure in the region of interest over a time period. A set of parameter signals representing values of the movement parameter within the structure during the time period is generated in response to the received signals. A color characteristic signal representative of a selected value larger than the mean value of the set of parameter signals is generated in response to the set of parameter signals. A color representation of the moving structure is displayed in response to the color characteristic signal.

Certain embodiments of the present invention afford an approach to visualize the color display of movement parameter values of moving structure greater than mean values in real-time with a degree of convenience and accuracy previously unattainable in the prior art.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

An embodiment of the present invention enables longitudinal tracking of moving structure and real time color visualization of peak parameters of the moving structure. As used herein, structure means non-liquid and non-gas matter, such as cardiac wall tissue. An embodiment of the present invention offers improved, real-time visualization and assessment of wall tissue function. The moving structure is characterized by a movement parameter, which means a parameter derived from movement of the structure, such as velocity or strain rate.

Figure 1:
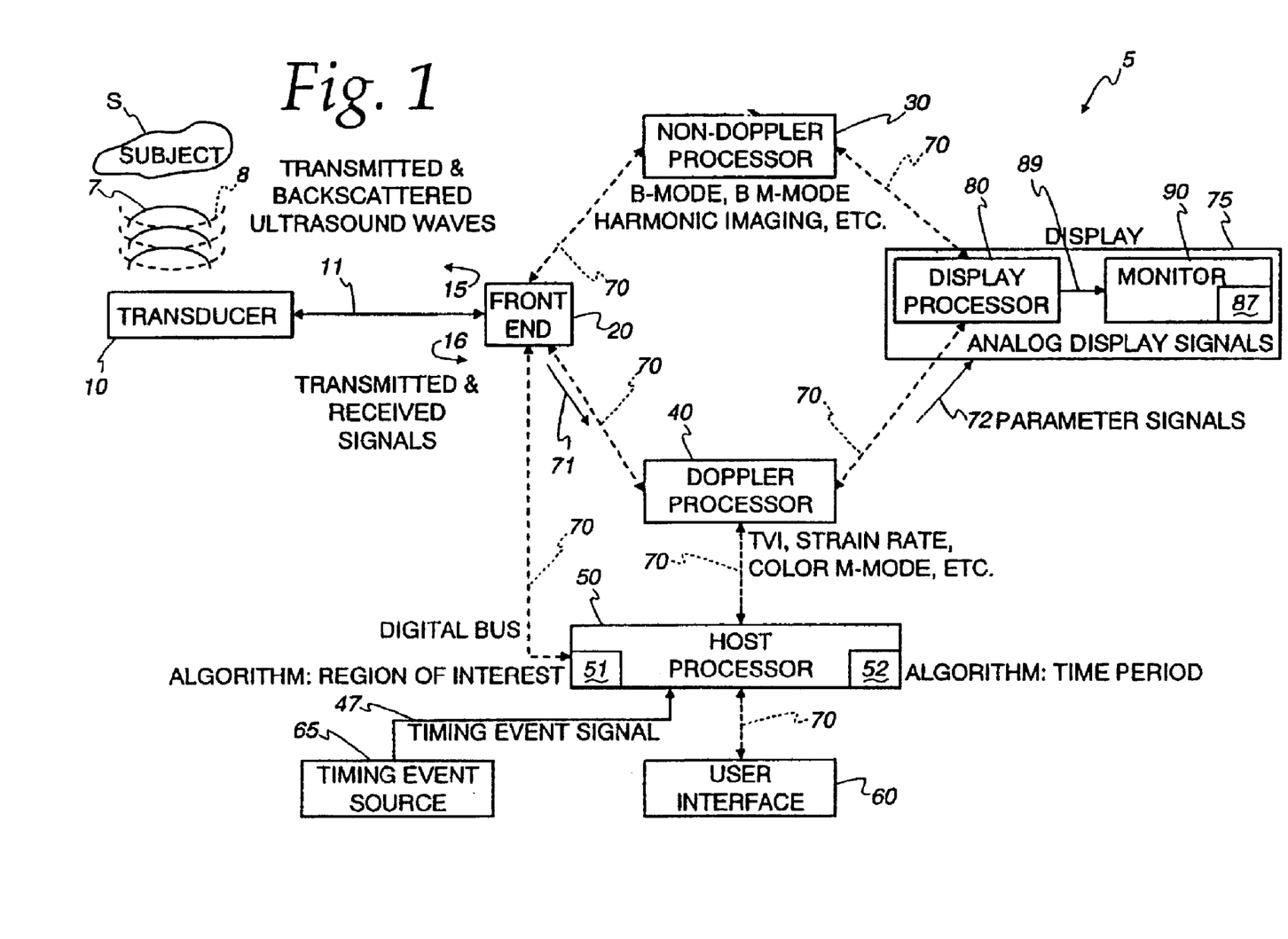
FIG. 1 is a schematic block diagram of an ultrasound machine in accordance with an embodiment of the present invention.

FIG. 1 is a schematic block diagram of an ultrasound machine 5 in accordance with an embodiment of the present invention. A transducer 10 is used to transmit ultrasound waves 7 (solid curves in FIG. 1) into a subject S by converting electrical analog signals 15 to ultrasonic energy and to receive ultrasound waves 8 (dashed curves in FIG. 1) backscattered from the subject S by converting ultrasonic energy to analog electrical signals 16. A front-end 20 comprising a receiver, transmitter, and beamformer, is used to create the necessary transmitted waveforms, beam patterns and receiver filtering techniques that are required for the various imaging modes. Front-end 20 performs the functions by converting digital data to analog data and vice versa. Front-end 20 interfaces at an analog interface to transducer 10 and interfaces at a digital interface over a digital bus 70 to a non-Doppler processor 30 and a Doppler processor 40 and a host processor 50. Digital bus 70 may comprise several digital sub-buses, each sub-bus having its own unique configuration and providing digital data interfaces to various parts of the ultrasound machine 5.

Non-Doppler processor 30 comprises amplitude detection functions and data compression functions used for imaging modes such as B-mode, B M-mode, and harmonic imaging. Doppler processor 40 comprises clutter filtering functions and movement parameter estimation functions used for imaging modes such as tissue velocity imaging (TVI), strain rate imaging (SRI), and color M-mode. The two processors, 30 and 40, accept digital data from the front-end 20, process the data into estimated mean values of amplitude and estimated mean values of movement parameters, and pass the values to a display 75 over digital bus 70. The estimated mean values may be created using the received signals in frequency bands centered at harmonics or sub-harmonics of the transmitted signals in a manner known to those skilled in the art.

Display 75 comprises scan-conversion functions, color mapping functions, and tissue/flow arbitration functions, performed by a display processor 80 which accepts digital parameter signals 72 from processors 30 and 40, processes, maps, and formats the digital data for display, converts the digital display data to analog display signals 89, and passes the analog display signals 89 to a monitor 90. Monitor 90 accepts the analog display signals 89 from display processor 80 and displays the resultant image 87 to the operator on monitor 90.

A user interface 60 allows user commands to be input by the operator to the ultrasound machine 5. User interface 60 comprises a keyboard, mouse, switches, knobs, buttons, track ball, and on screen menus (not shown).

Host processor 50 is the main, central processor of the ultrasound machine 5 and interfaces to various other parts of the ultrasound machine 5 through digital bus 70. Digital data and commands are transmitted and received between the host processor 50 and other various parts of the ultrasound machine 5. The functions performed by processor 50 could be performed by multiple processors or may be integrated into processors 30, 40, or 80, or any combination thereof.

Figure 2:
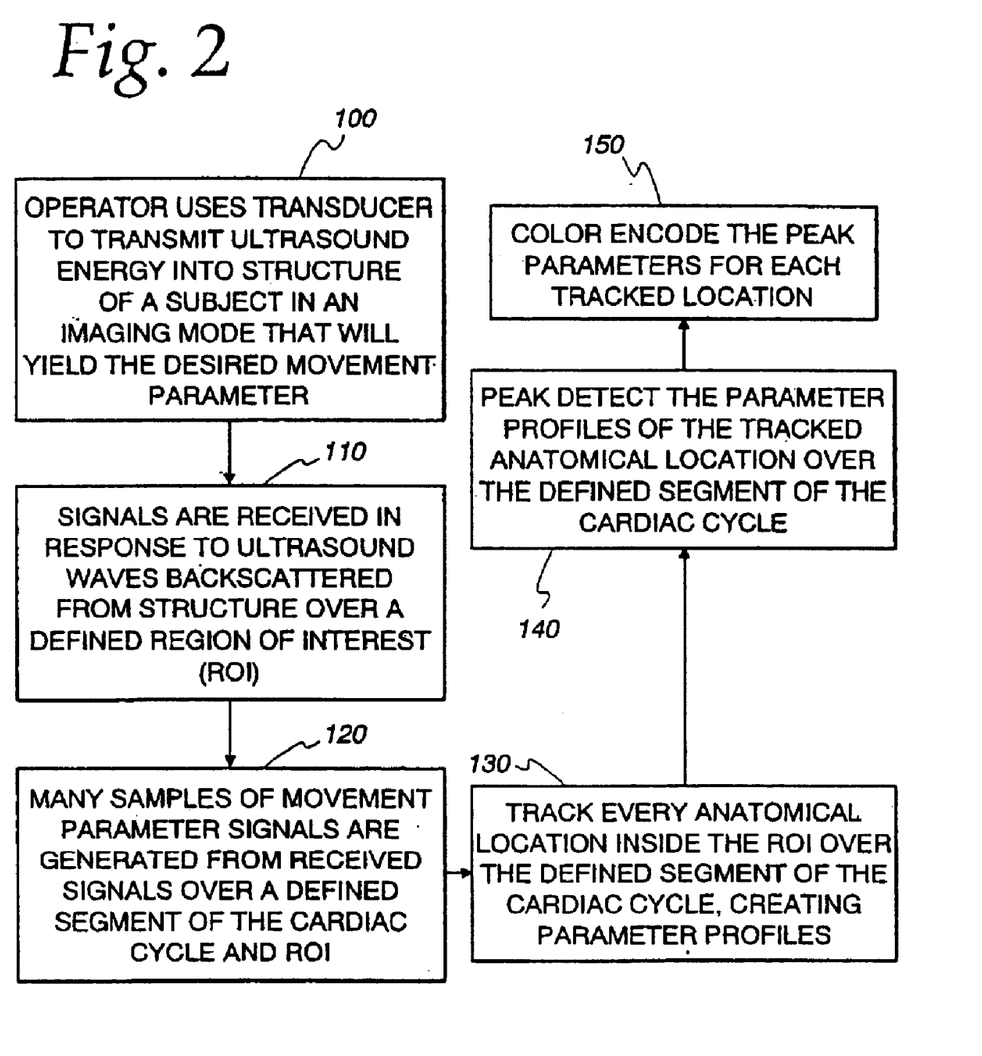
FIG. 2 is a flowchart of a method performed, at least in part, by the machine shown in FIG. 1 in accordance with an embodiment of the present invention.
Figure 7:
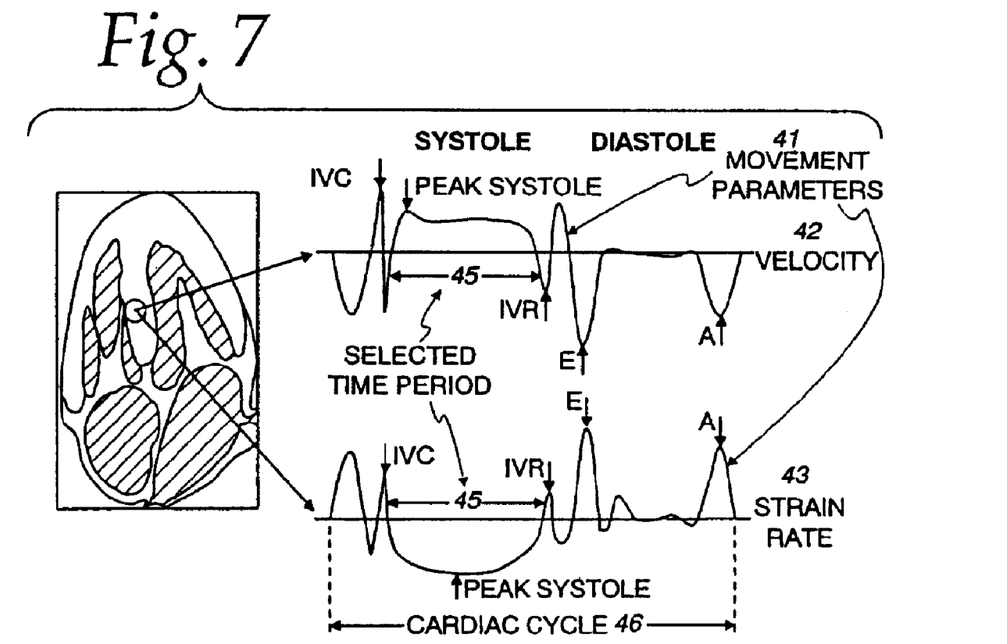
FIG. 7 is a schematic cross-sectional view of the heart shown in FIG. 6a also illustrating typical mean velocity and mean strain rate profiles as a function of time, measured longitudinally in an apical view in accordance with an embodiment of the present invention.

Referring to FIG. 2, in step 100 an operator uses transducer 10 to transmit ultrasound energy into the appropriate anatomical structure, such as cardiac tissue 105 (see FIG. 3), of the subject in an imaging mode (such as TVI or SRI) that will yield a desired movement parameter 41 (see FIG. 7) of the anatomical structure 105. As shown in FIG. 7, the movement parameter 41 typically comprises longitudinal estimates of mean tissue velocity 42 or mean tissue strain rate 43 parameters. The specification herein uses the example of tissue velocity imaging (TVI) to illustrate various embodiments of the present invention. Based on the specification, those skilled in the art may also provide an embodiment that employs tissue strain rate and other movement parameters.

Figure 3:
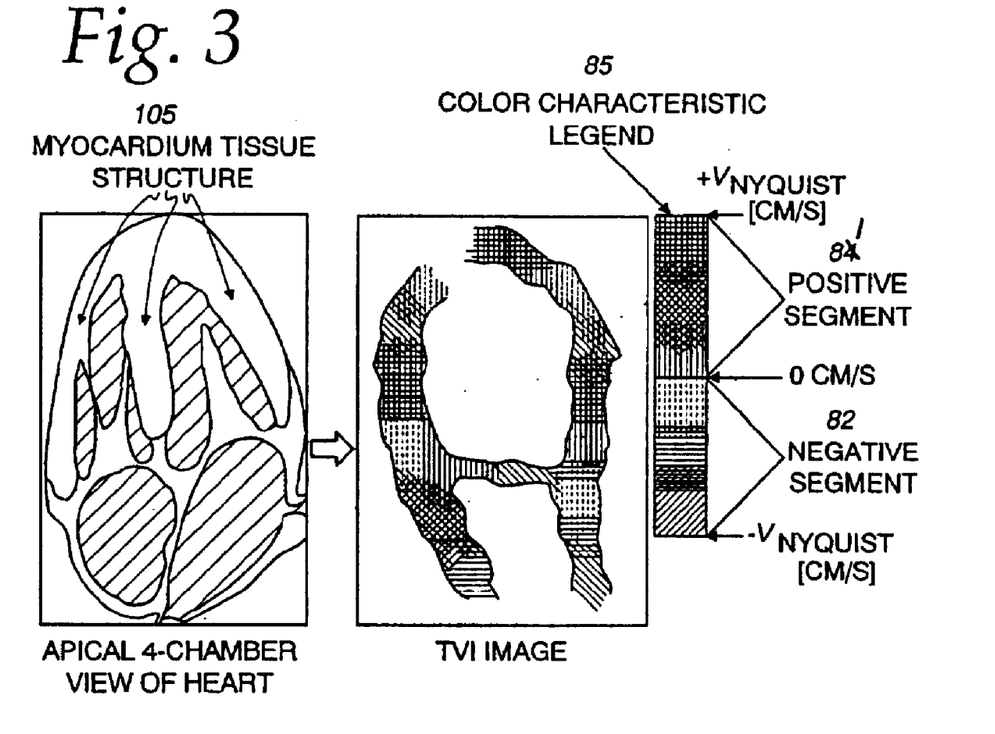
FIG. 3 illustrates the exemplary imaging mode of tissue velocity imaging (TVI) performed, at least in part, by the machine shown in FIG. 1 in accordance with an embodiment of the present invention.
Figure 4:
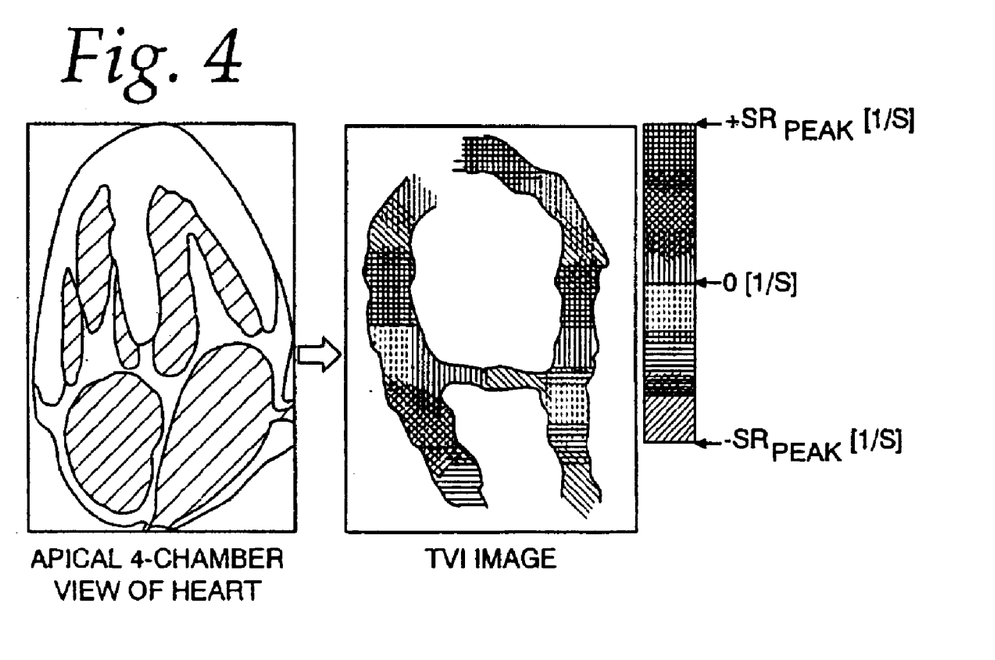
FIG. 4 illustrates the exemplary imaging mode of strain rate imaging (SRI) performed, at least in part, by the machine shown in FIG. 1 in accordance with an embodiment of the present invention.

Referring to FIG. 3, in TVI mode a fixed, continuous range of color hues is used to indicate positive velocities and a second fixed, continuous range of color hues is used to indicate negative velocities. Typically, red/yellow hues show anatomical motion towards the transducer 10 and blue/green hues show motion away from the transducer 10. The color hues are illustrated in the color characteristic legend 85 shown in FIG. 3. The various cross-hatchings and lines in the color characteristic legend 85 of FIG. 3 represent a continuous range of color hues. Going from the top of the color characteristic legend 85 to the bottom, the color hues transition from yellow to orange to red representing the positive velocity segment 81 of the color characteristic legend 85 and then violet to blue to green, representing the negative velocity segment 82 of the color characteristic legend 85. However, the color hues that make up the color characteristic legend 85 may be any continuous, semi-continuous, or discrete range of color hues that provide good discrimination between levels of the movement parameter 41. The portions of the color characteristic legend 85 in which cross-hatched lines intersect represent a blending of color hues.

Figure 6A:
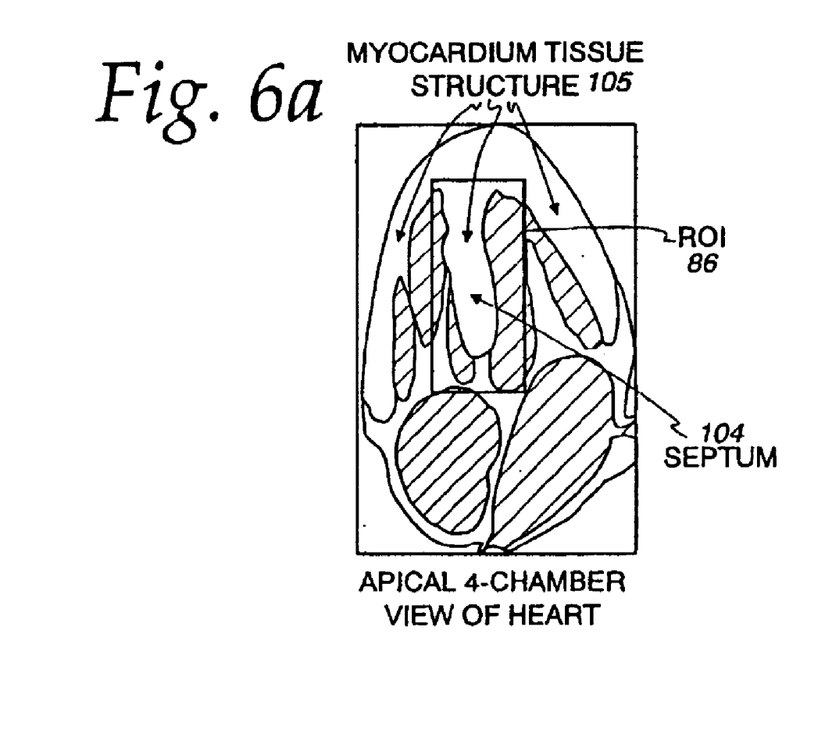
FIG. 6a is a schematic cross-sectional view of the human heart including myocardium tissue bounded by a region of interest (ROI) that is designated by the machine shown in FIG. 1 in accordance with an embodiment of the present invention.
Figure 6B:
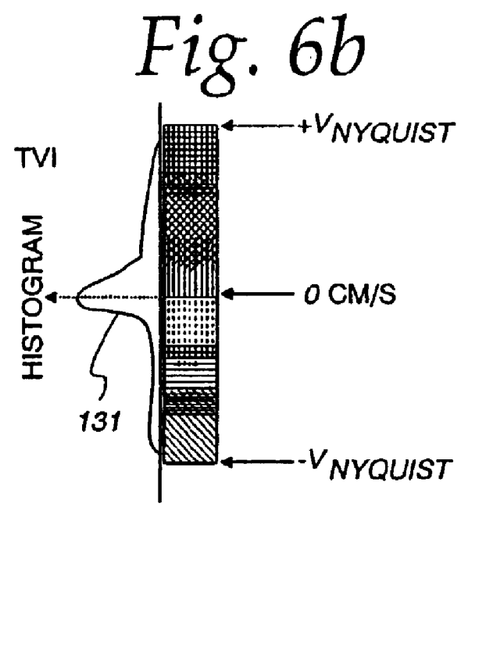
FIG. 6b is an exemplary histogram representing the frequency of occurrence of estimated mean velocity values of samples of tissue within the ROI of FIG. 6a in accordance with an embodiment of the present invention.

The histogram 131 of FIG. 6b illustrates how typical longitudinal mean velocity measurements in the myocardium of the heart 105 may be distributed. Lower positive and lower negative mean velocities, compared to the peak mean velocities, dominate the frequency distribution as is seen by the hump in the histogram 131. The peak mean velocities only occur for a short period of time. Also illustrated in FIG. 7 are typical velocities and strain rate values at specific anatomical points plotted as a function of time. Apical images contain a large spatial gradient in the mean velocities. Peak mean velocities are both spatially and temporally localized and represent only a minor part of the histogram 131.

In step 110 of FIG. 2, ultrasound energy is received into transducer 10 and signals are received into front-end 20 in response to ultrasound waves 8 backscattered from the structure 105 over an operator-defined region of interest (ROI) 86 (see FIG. 6a). The operator brings up a scaleable ROI 86 on monitor 90 through the user interface 60 to select a spatial or anatomical region to process such as the septum 104 of the heart (see FIG. 6a). The ROI may be chosen to cover the entire displayed image 87 if desired. Such a selection of an ROI 86 will force the subsequent processing to segment, track, and peak-detect the displayed image 87 for that specific region. The approach may, for example, be useful if the operator wants to provoke a good visualization of peak longitudinal myocardial velocities in a specific region. In other similar embodiments, the ROI 86 may be selected automatically or as a combination manual and automatic methods. For example, an algorithm 51 (see FIG. 1) for automatic identification of an ROI 86 may be designed and embedded in the host processor 50 to separate the myocardium from cavities. Well-known segmentation and thresholding techniques operating on the data of the movement parameter 41 may be used. The ROI 86 is automatically sized and positioned on display image 87 based on the results of the techniques.

Figure 5:
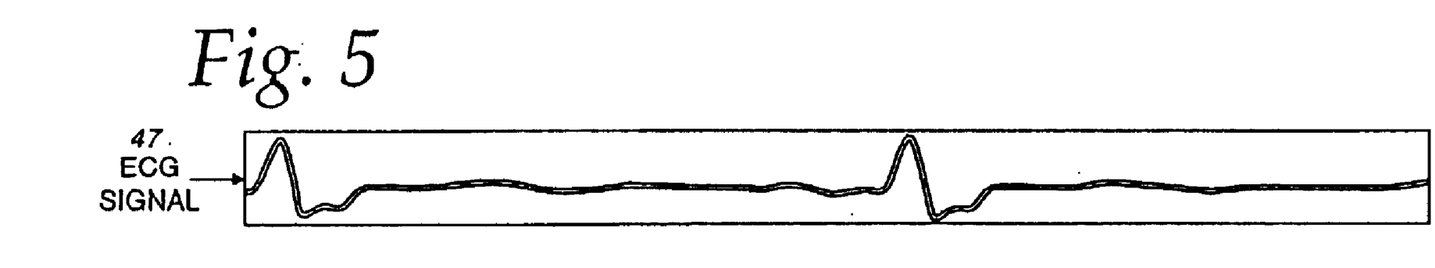
FIG. 5 illustrates the exemplary ECG signal used, in part, by the method in FIG. 2 in accordance with an embodiment of the present invention.
Figure 8:
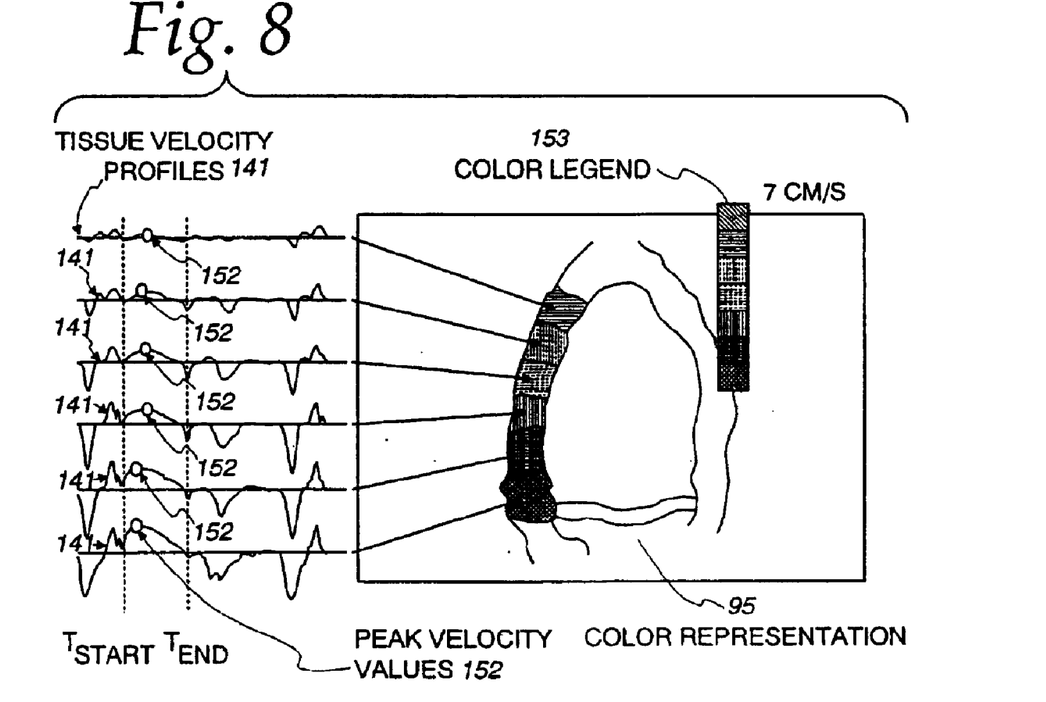
FIG. 8 illustrates the peak-detected velocity profiles and color encoding generated by the method shown in FIG. 2 which is executed, at least in part, by the machine shown in FIG. 1 in accordance with an embodiment of the present invention.

In step 120 of FIG. 2, received signals 71 are sent from front-end 20 to Doppler processor 40 over digital bus 70. Many samples of movement parameter signals 72, such as mean velocity 42 or mean strain rate 43, are generated from the received signals 71 over a segmented time period 45 and ROI 86 by Doppler processor 40. The operator selects, through the user interface 60, a desired time interval 45 to process, such as systole, which is a sub-interval of the cardiac cycle 46 (see FIG. 7). In FIG. 8, the time interval is designated by $T_{start}$ and $T_{end}$. The time interval is determined using well-known timing event sources 65 (FIG. 1) and techniques such as electro-cardiogram (ECG) techniques responsive to an ECG signal 47 (see FIG. 5) and/or characteristic signatures in the profiles of the movement parameter 41. It is also possible to derive timing events from signals of other sources such as phonocardiogram, pressure wave, pulse wave, or a respiratory signal. Those skilled in ultrasound know how to obtain such timing events from timing sources. Ultrasound modalities such as spectrum Doppler or M-modes may also be used to obtain timing information.

$T_{start}$ is typically selected by the operator as an offset from the R-event in the ECG signal. $T_{end}$ is set such that the time interval covers a selected portion of the cardiac cycle such as systole. It is also possible to select a time period 45 corresponding to the complete cardiac cycle 46. Another possibility is to limit the time period 45 to the systolic time period in order to display a color representation that is optimized for visualization of peak systolic parameters. Other sub-intervals of the cardiac cycle 46 may also be applied. FIG. 7 illustrates typical velocity and strain rate profiles which may be segmented into desired time periods based on profile signature characteristics. For reference, the profiles in FIG. 7 are annotated with the times corresponding to: IVC=isovolumetric contraction, IVR=isovolumetric relaxation, E=early diastolic velocity, and A=late diastolic velocity.

In other possible embodiments, the time interval could be selected automatically or as a combination of manual and automatic methods. For example, the time period 45 could be determined automatically with an algorithm 52 (see FIG. 1) embedded in host processor 50. The algorithm 52 may use well-known techniques of analyzing the profiles of the movement parameter 41, as shown in FIG. 7, looking for key profile signature characteristics and defining a time period 45 based on the characteristics, or similarly, analyzing the ECG signal 47.

Figure 9:
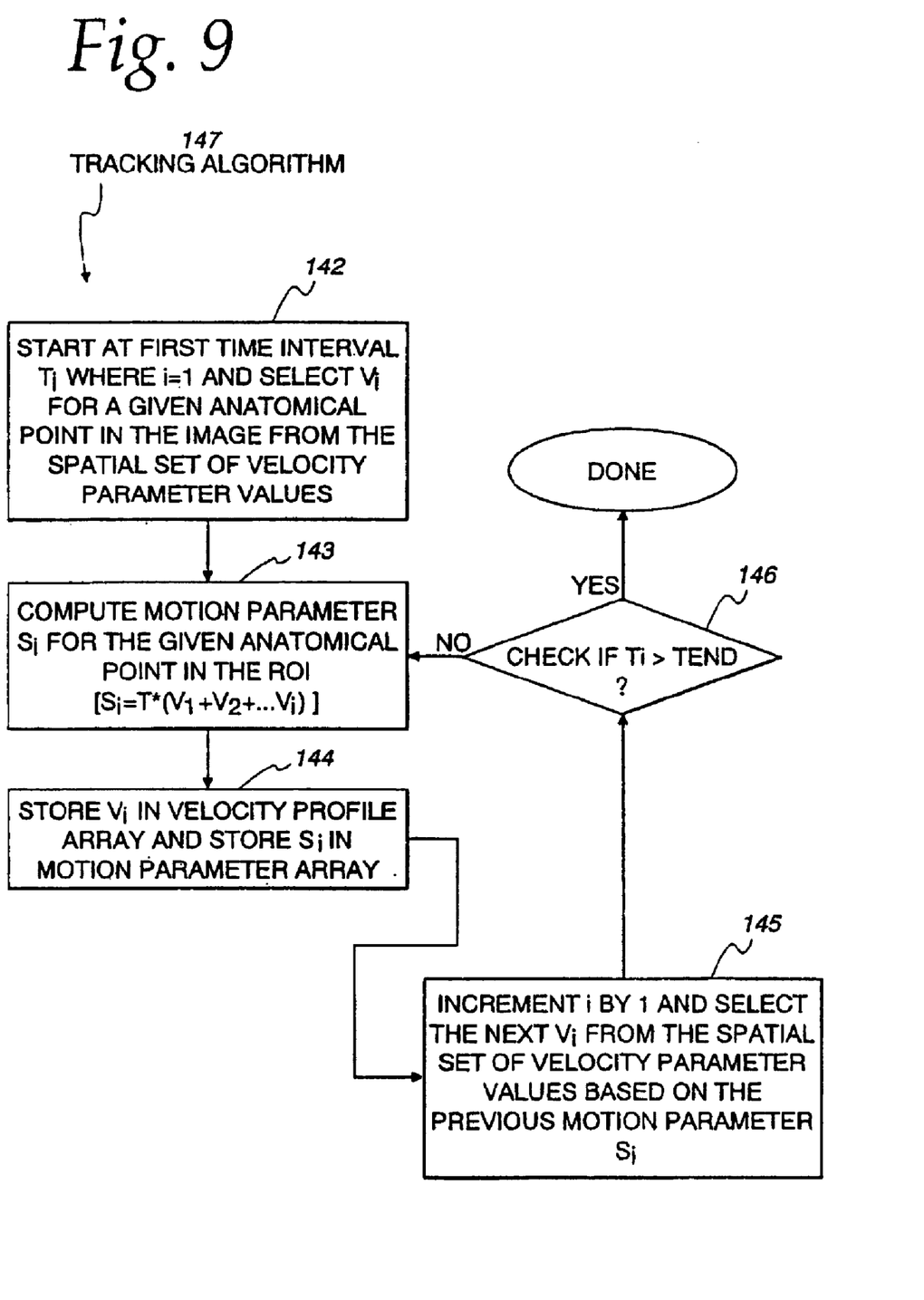
FIG. 9 is a flowchart of the longitudinal tracking function performed by the method shown in FIG. 2 and is executed, at least in part, by the machine shown in FIG. 1 in accordance with an embodiment of the present invention.

In step 130 of FIG. 2, the operator initiates, through user interface 60, real time tracking of every anatomical location inside the selected ROI 86 over the selected time period 45 of the cardiac cycle 46. The spatial set of parameter values representing the movement parameter 41 are sent from Doppler processor 40 to host processor 50, where a tracking function 147 is applied to the values of the movement parameter 41. FIG. 9 is a flow chart of the tracking function 147.

Figure 10:
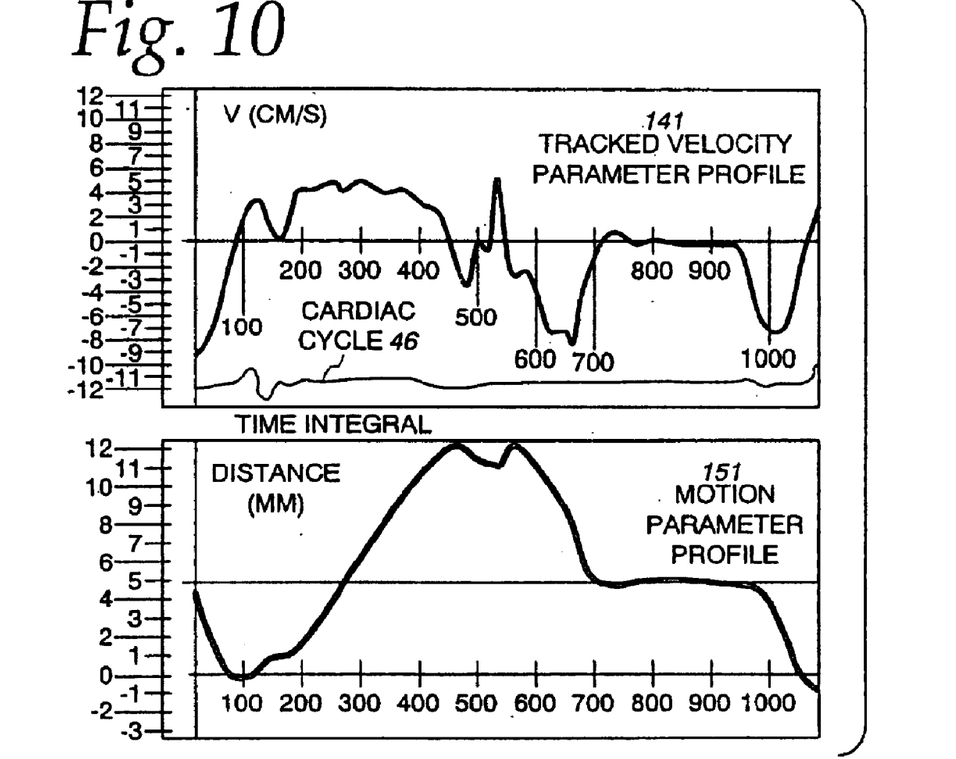
FIG. 10 illustrates a longitudinal tracking function performed by the method shown in FIG. 2 and flowchart shown in FIG. 9 which is executed, at least in part, by the machine shown in FIG. 1 in accordance with an embodiment of the present invention.

As an introduction to the tracking function 147, a tracked velocity parameter profile 141 ($V_1, V_2, \ldots, V_n$) for a given sampled anatomical location in the myocardium 105, is created over the time period $T_{start}$ to $T_{end}$ (see FIG. 8) by converting the spatial velocity estimates into a motion parameter profile 151 in time (see FIG. 10) using host processor 50. The series of time integrals ($S_1, S_2, \ldots, S_n$) is computed where:

$$S_i = T^*(V_1 + V_2 + \ldots + V_i) \qquad \text{[Equation 1]}$$

and where T is the time delay between two consecutive velocity measurements (T is typically based on the frame rate of the imaging mode). $S_i$ is the longitudinal distance in millimeters (from reference time zero location) that a sample of tissue in the myocardium has moved at time segment $T_i$, thus allowing the isolated tissue sample to be tracked longitudinally (along the ultrasound beam) over the time interval $T_{start}$ to $T_{end}$ by host processor 50. The tracking function estimates the new anatomical locations of the tracked sample tissue after every time segment $T_i$ and determines tracked velocities (or other quantitative movement parameters) at the new anatomical locations for each location in the selected ROI 86. The upper-most part of FIG. 10 shows a resultant tracked velocity parameter profile 141 of an anatomical location in an image as a function of time for a complete cardiac cycle 46. The lower-most part of FIG. 10 shows the corresponding resultant longitudinal motion parameter profile 151 (integrated velocity profile, $S_1, S_2, \ldots, S_n$) of the same anatomical location in the image. Motion along the ultrasound beam may be accurately tracked with the technique allowing the appropriate velocity parameter profiles to be generated for the corresponding anatomical locations. The tracked quantitative parameter profile 141 for each anatomical location is stored in the memory of host processor 50 as a sampled array of quantitative parameter values. As a result, the stored quantitative parameter profile history corresponds to each anatomical location, instead of just a spatial location in the image.

Two-dimensional velocity estimation is necessary for accurate tracking when a substantial part of the motion of the structure is orthogonal to the beam. Other tracking techniques may be employed as well.

As an alternative to tracking, spatial movement parameter profiles may be constructed by the host processor 50 from the values of the movement parameter and correlated to fixed spatial locations in the image instead of to anatomical locations. Subsequent peak-detection may then be performed at fixed spatial locations over the time period.

The specific steps of the preferred tracking function 147 are now described for a given anatomical location in the ROI 86. The methodology requires that, at a minimum, a spatial set of velocity parameter values is estimated in Step 120 of FIG. 2 in order for the motion values Si to be calculated for tracking. The velocity values are generated by Doppler processor 40 in a well known manner.

In step 142 of tracking function 147, processor 50 selects $V_i$ for a given anatomical location in the image from a spatial set of velocity parameter values in the ROI 86 corresponding to time interval $T_i$ where i=1 ($T_1$ is $T_{start}$).

In step 143 of tracking function 147, processor 50 computes the motion parameter $S_i$ for the given anatomical location in the ROI, as $$S_i = T^*(V_1 + V_2 + \ldots + V_i) \qquad \text{[Equation 1]}$$

(Note that for i=1, $S_1 = T^*V_1$)

In step 144 of tracking function 147, processor 50 stores $V_i$ in tracked velocity parameter profile array 141 and $S_i$ is stored in motion parameter profile array 151.

In step 145 of tracking function 147, i is incremented by one (corresponding to the next sample time, T seconds later) and the next $V_i$ is selected from the spatial set of velocity parameter values based on the motion parameter $S_i$ previously computed ($S_i$ represents the longitudinal spatial movement in mm of the anatomical location over time interval i*T).

In step 146 of tracking function 147, the function checks to see if $T_{end}$ has been exceeded. If, $T_{end}$ has not been exceeded, the function proceeds back to Step 143 and computes the next motion parameter value $S_i$ in the series using Equation 1. The iterative process is followed until the full arrays of tracked velocity profile parameters and motion profile parameters have been created and stored over the complete time interval $T_{start}$ to $T_{end}$.

The tracking function 147 is performed simultaneously for each anatomical location in the ROI 86.

In step 140 of FIG. 2, the stored tracked movement parameter profiles 141 (e.g. longitudinal mean velocity profiles) for each anatomical location are peak-detected over the time interval $T_{start}$ to $T_{end}$ by the host processor 50. A peak-detection function in host processor 50 simply picks the largest positive or negative value in a given tracked movement parameter profile array (see FIG. 8). If both positive and negative profile peaks exist in the time interval $T_{start}$ to $T_{end}$, a decision is made as to which value to extract as the peak value 152 over the interval. In an embodiment of the present invention, the largest absolute value is extracted as the peak value 152 and its sign (positive or negative) is maintained as well. As an alternative, only the largest positive peak value or only the largest negative peak value may be extracted. The functionality is part of the decision logic of the peak-detection function in host processor 50.

Other alternative peak-detection functions may be substituted as well. For example, an alternative function could recognize and exclude unwanted events from the tracked movement parameter profile such as IVC or IVR peaks.

The peak-detection function is performed simultaneously for each anatomical location in the ROI 86.

Care should be taken by the operator to adjust the Nyquist frequency of the imaging mode such that aliasing does not occur. With aliasing present in the data, erroneous peak detected results may occur. Alternatively, well known automatic aliasing correction techniques may be employed.

Figure 11:
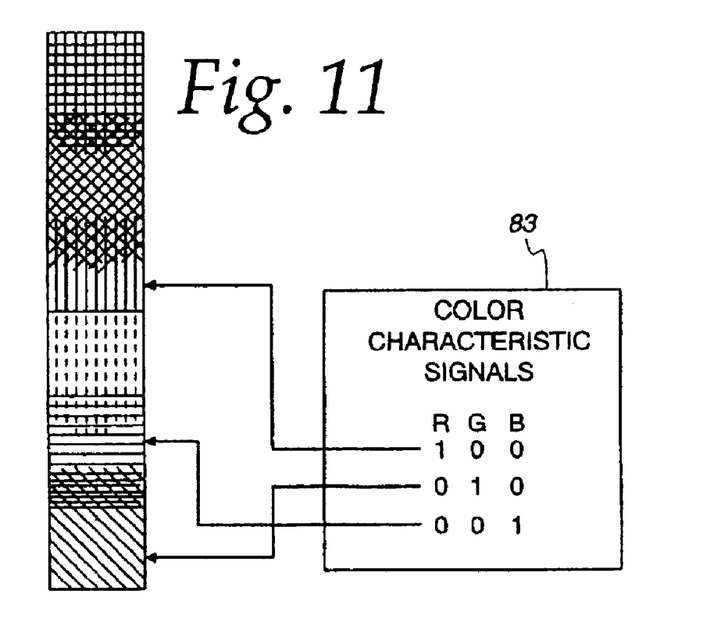
FIG. 11 illustrates the color characteristic signals in terms of RGB values and how the values relate to the color characteristic legend in accordance with an embodiment of the present invention.

In step 150 of FIG. 2, the extracted peak parameter value 152 for each tracked anatomical location is used by display processor 80 to color encode the associated location in the image. The extracted peak parameter values 152 may either be color encoded with the same color encoding (color mapping table) as the underlying TVI or SRI imaging mode, or a dedicated color encoding may be devised for the peak parameter display. Clinical work on peak systolic velocities shows that it is advantageous to design a color encoding such that quantitative values may be inferred directly from the color encoding. FIG. 8 illustrates the results of color encoding over a myocardial segment of the heart using a pre-defined, discrete color mapping table where N discrete colors are used to visualize the peak velocities. In the example, seven discrete color hues are used to separate between velocities: 0–1 cm/sec, 1–2 cm/sec, and up to 6–7 cm/sec (see color legend 153 of FIG. 8). The number of discrete colors may be increased over the velocity scale in order to get a finer separation of peak velocities. The color hues are typically represented in memory as red, green, blue (RGB) values as shown in FIG. 11. The RGB values constitute the color characteristic signals 83. The RGB values may be represented as normalized values between 0 and 1, as shown in FIG. 11. Therefore, to represent a perfectly red hue, the RGB values would be (1 0 0). For a perfectly green hue, the RGB values would be (0 1 0), and for blue (0 0 1). Any other color hue may be represented by various combinations of RGB values. For example, RGB values of (0.5 0.8 0.3), are a combination of unequal parts of red, green, and blue hues each with a different weighting, resulting in some new color hue. An RGB combination of (1 1 1) yields a perfectly white hue and an RGB combination of (0 0 0) yields a perfectly black hue.

As an alternative, peak detection may be performed after each new tracked element in the tracked movement parameter profile array is added or after each new spatial element is added to the spatial movement parameter profile, allowing a constant update of the displayed peak value within the time interval $T_{start}$ to $T_{end}$.

The velocity corresponding to the velocity cutoff (Nyquist velocity) for the color encoding of the highest velocities may be preset in order to relate the velocities to normal physiological values. Typically, a normal physiological value may be used for the preset. The setting will depend on the image view and the stress level in a stress echo exam. If for instance the normal basal peak velocity is selected, one can determine whether a patient has normal longitudinal function at the given stress level simply by checking whether the color corresponding to the highest velocity index appears in the basal segment. Different anatomical segments may be addressed in a similar manner. A reduction in longitudinal function may be quantified by evaluating the percentage of the normal velocity range that is actually observed.

FIG. 7 illustrates several peaks (IVR, IVC, E, A, peak systole) in both velocity profiles and strain rate profiles that may have clinical interest. The peak values may be studied separately by setting of the time interval that is used for the analysis.

In SRI, exactly the same method as for TVI may be followed to display peak mean strain rate values. In addition, it may be possible to reserve a unique color hue for small spatial deformations under a preset strain rate threshold. The described method should then be limited to operate on the strain rate values exceeding the threshold value. Other peak quantitative parameters may be estimated, extracted, and similarly encoded for display, as well.

Similarly, more than one parameter may be extracted from the same cardiac cycle and combined for display. An example is the computation of ratio images where the process described herein for determination of peak parameters is performed over two time periods and the ratio between the two peak values is used to color encode the spatial or tracked anatomical locations. Ratio images remove the angle dependence for example, tissue velocity imaging because the unknown cosine modulation caused by the angle of incidence is the same in both measurements. Examples of clinically interesting ratio images include:

VR velocity/systolic velocity: indicates the relative amount of motion in the isovolumetric relaxation period relative to the systolic motion. Clinical research indicates that high ratios can correlate with pathology.

Systolic velocity/E velocity: may be used to detect blunted relaxation.

E velocity/A velocity: E/A reversals have received much clinical interest.

Ratios of other combinations may be calculated and displayed as well. For example, it may be useful to compute ratios between time integrated values and peak parameter values for a given time period. The ratio may contain information related to acceleration in the selected time period.

Embodiments of the present invention may be applied to any imaging mode of the ultrasound machine 5 for moving structure, for any estimated peak parameter (e.g. velocity, strain rate, power, amplitude, etc.).

In summary, certain embodiments of the present invention afford an approach to generating an image responsive to moving structure by displaying selected peak values or ratios of peak values, of signals representative of the moving structure, in a color format.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In an ultrasound machine for generating a display responsive to moving structure within a region of interest of a subject by displaying at least one color characteristic related to a movement parameter of the structure, apparatus for displaying the color characteristic comprising:
   a front-end arranged to transmit ultrasound waves into the structure and to generate received signals in response to ultrasound waves backscattered from the structure in the region of interest over a time period;
   a processor responsive to the received signals to generate a set of parameter signals representing values of the movement parameter within the structure during the time period and responsive to the set of parameter signals to generate a color characteristic signal representative of a selected value larger than the mean value of the set of parameter signals; and
   a display arranged to display a color representation of the moving structure in response to the color characteristic signal.

2. The apparatus of claim 1 wherein the moving structure comprises cardiac tissue.

3. The apparatus of claim 1, wherein the movement parameter comprises one of velocity and strain rate.

4. The apparatus of claim 1 wherein the color characteristic comprises hue.

5. The apparatus of claim 1, wherein the set of parameter signals comprises a set of mean values of the parameter signals.

6. The apparatus of claim 5, wherein the selected value comprises the largest mean value within the set of mean values.

7. The apparatus of claim 1 wherein the time period comprises at least a portion of a cardiac cycle selectable by a user of the machine, said portion including systole, diastole, IVC, IVR, E-wave, and A-wave.

8. The apparatus of claim 7 wherein the portion of the cardiac cycle is selectable from one of a phonocardiogram, a pressure wave, a pulse wave, and a respiratory signal.

9. The apparatus of claim 1 wherein the processor generates a set of motion parameter profiles and a set of tracked movement parameter profiles over the time period corresponding to a set of sampled anatomical locations within the region of interest.

10. The apparatus of claim 1 wherein the time period comprises a first time period and a second time period, wherein the set of parameter signals comprises a first set of parameter signals representing first values of the movement parameter corresponding to the first time period and a second set of parameter signals representing second values of the movement parameter corresponding to the second time period, and wherein the processor generates a color characteristic signal representative of the ratio of at least a first value within the first set of parameter signals and a second value within the second set of parameter signals.

11. In an ultrasound machine for generating a display responsive to moving structure within a region of interest of a subject by displaying at least one color characteristic related to a movement parameter of the structure, a method of displaying the color characteristic comprising:

transmitting ultrasound waves into the structure;

generating received signals in response to ultrasound waves backscattered from the structure in the region of interest over a time period;

generating a set of parameter signals representing values of the movement parameter within the structure during the time period in response to the received signals;

generating a color characteristic signal representative of a selected value larger than the mean value of the set of parameter signals in response to the set of parameter signals; and displaying a color representation of the moving structure in response to the color characteristic signal.

12. The method of claim 11 wherein the moving structure comprises cardiac tissue.

13. The method of claim 11, wherein the movement parameter comprises one of velocity and strain rate.

14. The method of claim 11 wherein the color characteristic comprises hue.

15. The method of claim 11, wherein the set of parameter signals comprises a set of mean values of the parameter signals.

16. The method of claim 15, wherein the selected value comprises the largest mean value within the set of mean values.

17. The method of claim 11 wherein the time period comprises at least a portion of a cardiac cycle selectable by a user of the method.

18. The method of claim 17 wherein the portion of the cardiac cycle is selectable from one of a phonocardiogram, a pressure wave, a pulse wave, and a respiratory signal.

19. The method of claim 11 wherein said generating a set of parameter signals comprises generating a set of motion parameter profiles and a set of tracked movement parameter profiles over the time period corresponding to a set of sampled anatomical locations within the region of interest.

20. The method of claim 11 wherein the time period comprises a first time period and a second time period, wherein the set of parameter signals comprises a first set of parameter signals representing first values of the movement parameter corresponding to the first time period and a second set of parameter signals representing second values of the movement parameter corresponding to the second time period, and wherein said generating a color characteristic signal comprises generating a color characteristic signal representative of the ratio of at least a first value within the first set of parameter signals and a second value within the second set of parameter signals.

* * * * *